(12) United States Patent
Ponsi et al.

(10) Patent No.: US 8,435,199 B2
(45) Date of Patent: May 7, 2013

(54) THERAPEUTIC BOOTS STABILIZATION WEDGE

(75) Inventors: Lawrence G. Ponsi, Wheeling, IL (US); Jeffrey K. Crum, Cottageville, WV (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 13/413,926

(22) Filed: Mar. 7, 2012

(65) Prior Publication Data

US 2012/0179082 A1 Jul. 12, 2012

Related U.S. Application Data

(63) Continuation of application No. 13/242,132, filed on Sep. 23, 2011, which is a continuation of application No. 11/855,560, filed on Sep. 14, 2007.

(51) Int. Cl.
*A61F 5/00* (2006.01)
(52) U.S. Cl.
USPC .......... 602/27; 602/23; 602/62; 602/65; 128/882; 36/140

(58) Field of Classification Search .......... 602/23, 602/27, 62, 65, 28, 29, 60, 61, 66, 75; 128/882, 128/869, 892; 36/140, 142–144
See application file for complete search history.

(56) References Cited

U.S. PATENT DOCUMENTS

| | | | |
|---|---|---|---|
| 4,745,917 A * | 5/1988 | Hasty et al. | 602/63 |
| 6,585,674 B2 * | 7/2003 | Toda | 602/62 |
| 8,152,749 B2 | 4/2012 | Ponsi et al. | |

OTHER PUBLICATIONS

U.S. Patent and Trademark Office's Office Action dated Jul. 20, 2012 for U.S. Appl. No. 13/242,132.

* cited by examiner

*Primary Examiner* — Patricia Bianco
*Assistant Examiner* — Keri J Nelson
(74) *Attorney, Agent, or Firm* — Brinks Hofer Gilson & Lione

(57) ABSTRACT

A device for stabilizing a limb, typically when the limb is in a therapeutic boot. A wedge-shaped stabilization block includes an outwardly-extending tether. A fastener in the form of spaced fastener elements is located on the tether for securing the stabilization block in place.

18 Claims, 4 Drawing Sheets

THERAPEUTIC BOOTS STABILIZATION WEDGE

CROSS-REFERENCE TO RELATED APPLICATION

This application is a continuation of co-pending U.S. patent application Ser. No. 13/242,132, filed Sep. 23, 2011, which is a continuation of co-pending U.S. patent application Ser. No. 11/855,560, filed Sep. 14, 2007. The entire contents of these applications are incorporated herein by reference.

BACKGROUND

This invention relates to stabilization of a limb in a patient setting, and in particular to a device for use as an adjunct for limb stabilization.

In U.S. Pat. No. 7,798,984, the entire contents of which are incorporated herein by reference, which issued Sep. 21, 2010 and is assigned to the assignee of the present application, a heel ulcer prevention and cushioning boot is disclosed and described. The boot provides heel support and comfort, as well as proper positioning of a patient's leg to avoid creating other problems, such as ulcers.

It may be desirable to provide a device for maintaining or promoting a desired orientation of a limb while providing additional stabilization to maintain the proper limb orientation. The present invention provides that additional stabilization.

SUMMARY

The invention is directed to a device for stabilizing a limb, comprising a stabilization block, a tether secured to and extending from the block, and a fastener for securing the stabilization block in place for supporting the limb.

In accordance with one form of the invention, the stabilization block is elongated and generally triangular in cross-section. The tether comprises an elongated strap, with the fastener comprising a pair of spaced fastener elements on the strap. In one form of the invention, the fastener elements comprise hook-and-loop fasteners which are located substantially at opposite ends of the strap, with one located proximate the block and the other located at the opposite end of the tether.

In another form of the invention, a pair of stabilization blocks is provided, with the blocks being spaced apart and with the tether extending between and secured to the respective blocks.

BRIEF DESCRIPTION OF THE DRAWINGS

The invention is described in greater detail in the following description of examples embodying the best mode of the invention, taken in conjunction with the drawing figures, in which.

DETAILED DESCRIPTION

Figure 1:
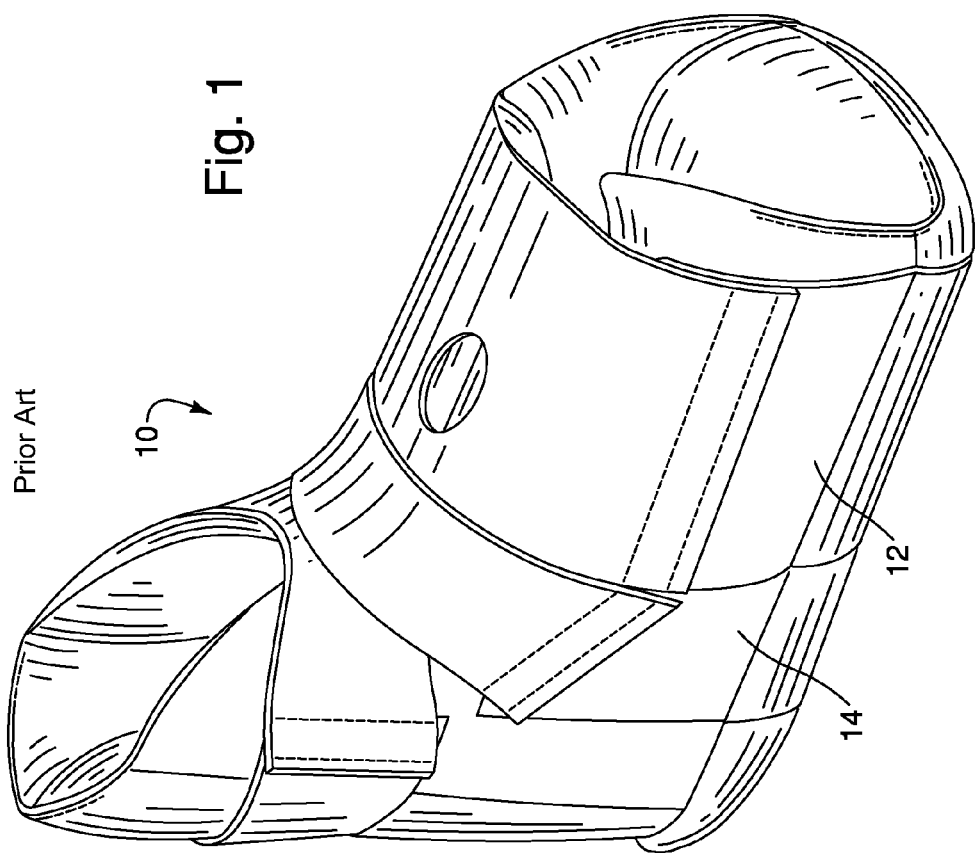
FIG. 1 is a perspective view of a therapeutic boot for which the invention of the present application is particularly suitable.

The stabilization wedge shown in the figures and described herein is particularly suitable for use in combination with a therapeutic boot, such as the boot 10 illustrated in FIG. 1. As disclosed in U.S. Pat. No. 7,798,984, issued Sep. 21, 2010, the entire contents of which are incorporated herein by reference, the boot 10 includes a leg engaging portion and a foot engaging portion and a leg-accepting aperture extending along the front side of the boot. The boot 10 includes hook-and-loop fastener segments 12 and 14 that may be coupled with the stabilization wedge shown in the figures, as is described below in more detail.

Figure 2:
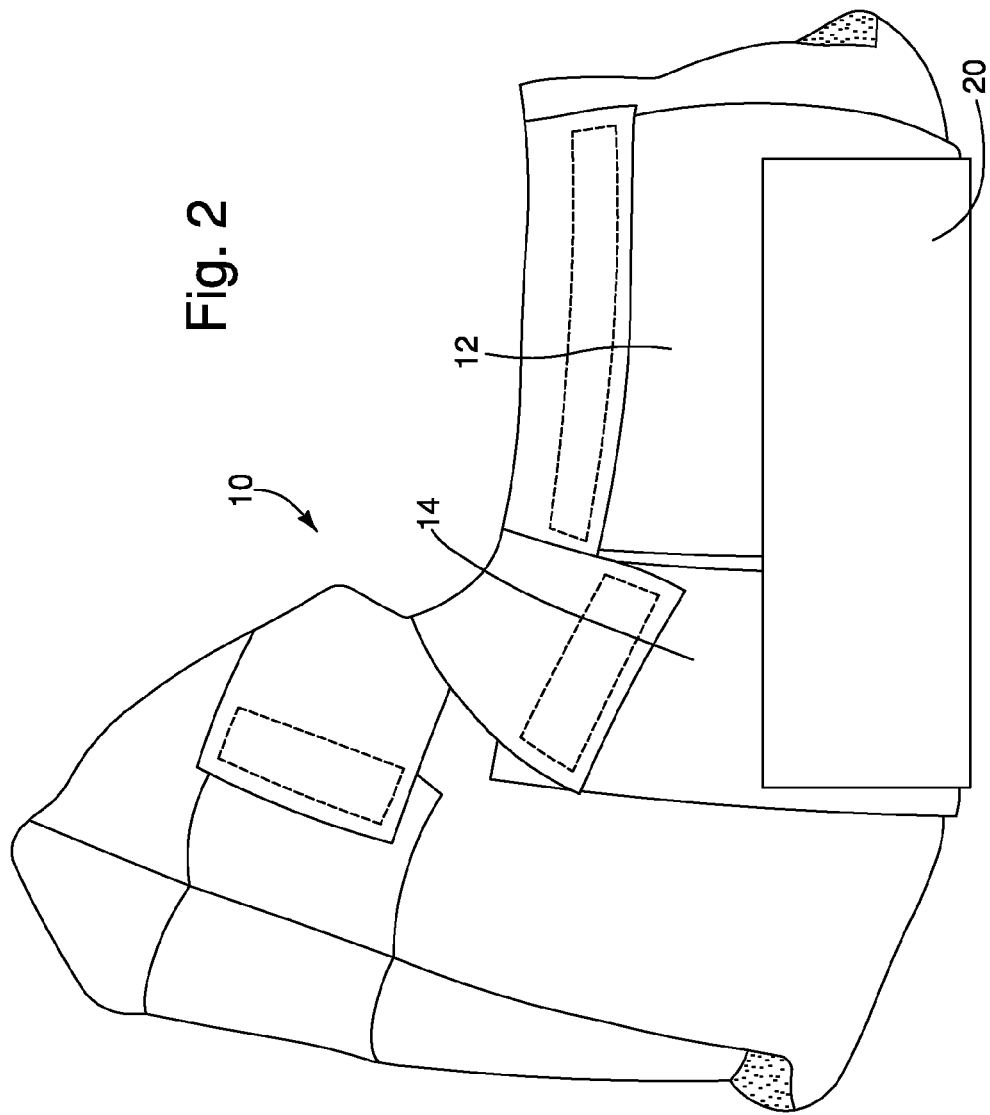
FIG. 2 is an elevational view of the boot of FIG. 1, having the stabilization wedge of the invention in place.
Figure 3:
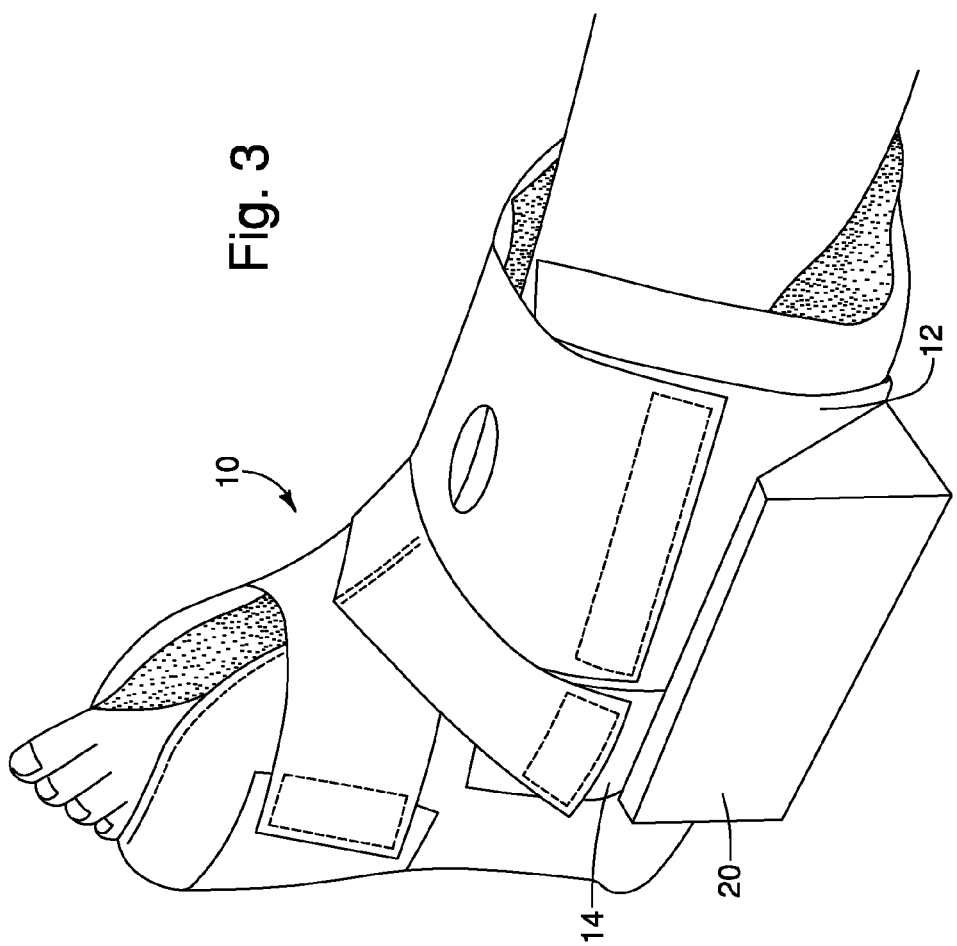
FIG. 3 is a perspective view similar to FIG. 1, with the stabilization wedge in place and showing how a patient's leg is supported.
Figure 4:
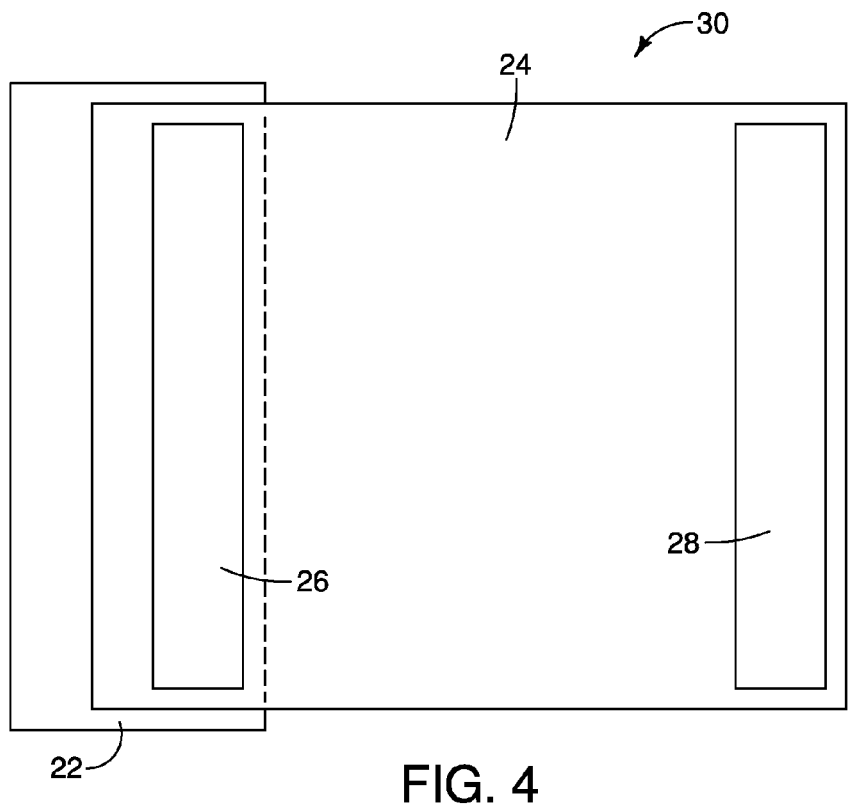
FIG. 4 is a top plan view of the stabilization wedge.
Figure 5:
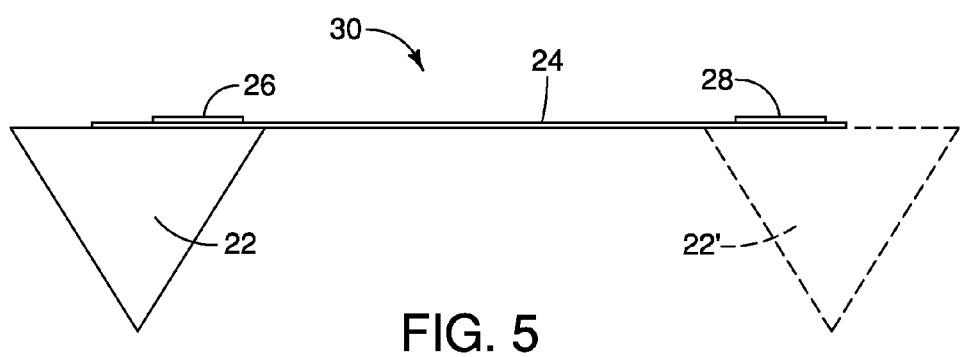
FIG. 5 is an elevational view of the wedge of FIG. 4.

A stabilization block 20 is shown in FIGS. 2 and 3, and an alternative embodiment stabilization block 22 is shown in FIGS. 4 and 5. The block 20 shown in FIGS. 2 and 3 differs from the block 22 shown in FIGS. 4 and 5 in the particular cross-sectional configuration. As shown in FIG. 3, the block 20 is generally trapezoidal in cross-section, while the block 22 shown in FIGS. 4 and 5 is generally triangular in cross section. Other shapes of the blocks 20 and 22 will be apparent to one skilled in the art, and the invention is not limited to simply a trapezoidal or triangular cross-section.

A tether 30 is secured to and extends from both block 20 and block 22. The tether 30 shown in the figures comprises an elongated strap 24, and may be secured to the respective block 20 or 22 by any means, such as sonic welding, adhesives, or any other means of forming a permanent connection between the block 20 or 22 and the elongated strap 24. The strap 24 shown in the drawings is generally flexible, and can be made of any suitable material, such as plastic or fabric. The block 20 or 22 shown in the drawings is substantially rigid, and can be formed of any suitable material, such as high density foam, plastic or the like.

As shown in the drawing figures, the blocks 20 and 22 are elongated and for fastening to the boot 10, a fastener is provided in the form of a pair of spaced fastener elements 26 and 28 on the strap 24. The fastener elements 26 and 28 complement the fastener segments 12 and 14, thus one of the segments 12 and 14 or elements 26 and 28 is preferably a hook element, while the other of the fastener segments 12 and 14 and fastener elements 26 and 28 is a loop element. Thus, when the block 20 or 22 is applied to the boot 10 as illustrated in the drawing figures, the hook and loop elements engage and hold the block 20 or 22 in place.

As shown in the figures, the fastener elements 26 and 28 are located substantially at opposite ends of the strap 24. The spacing of the fastener elements 26 and 28 is such to advantageously engage the fastener segments 12 and 14. As illustrated, the fastener element 26 is located proximate the stabilization block 20 or 22, and the fastener element 28 is located on the elongated strap 24 opposite the fastener element 26.

While the fastener elements 26 and 28 shown in the figures are hook-and-loop fastener segments to advantageously engage the hook-and-loop fastener segments 12 and 14, other types of fastener elements can be employed, as will be evident to one skilled in the art. Permanent fasteners, such as adhesives, can be utilized, as well as other types of temporary connection to the boot, such as various kinds of fasteners. The type of connection will be dictated by whether the user wishes a more permanent type of connection, or a readily removable type of connection.

As is evident from the figures and the disclosure herein, the stabilization block 20 or 22 may be used on either side of the boot 10. If desired, the blocks 20 or 22 can be doubled, that is, instead of a single block proximate the fastener element 26, there can be a second block proximate the fastener element 28. Thus, both sides of the boot 10 can be stabilized if needed.

The shape of the block 20 or 22 can vary depending upon the nature of the boot 10 and the use in connection with the boot. While two types of blocks 20 and 22 have been illustrated and described, it will be evident that other shapes will perform the stabilization functions as explained.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A device for stabilizing a limb, comprising:
   a. a therapeutic boot configured to receive and cushion the limb comprising a leg engaging portion, a foot engaging portion, and a leg-accepting aperture extending along a front side of the therapeutic boot,
   b. a stabilization block configured to impede rotation of the limb,
   c. a tether secured to and extending from the stabilization block, the tether configured to be coupled with the limb, and
   d. a fastener configured to couple the stabilization block with the therapeutic boot.

2. The device according to claim 1, in which the fastener is configured to be removably secured to the therapeutic boot.

3. The device according to claim 1, in which the stabilization block is elongated and generally trapezoidal in cross-section.

4. The device according to claim 1, in which the stabilization block is elongated and generally triangular in cross-section.

5. The device according to claim 1, in which the fastener comprises a pair of fastener elements spaced apart from each other.

6. The device according to claim 1, in which the fastener comprises at least one of a hook element and a loop element.

7. The device according to claim 1, wherein the tether includes a proximal surface and a distal surface, wherein the proximal surface is closer to the limb than the distal surface, and wherein the fastener is disposed on the proximal surface.

8. The device according to claim 7, wherein the stabilization block is disposed on the distal surface of the tether.

9. A device for stabilizing a limb, comprising:
   a. a therapeutic boot configured to receive and cushion the limb comprising a leg engaging portion, a foot engaging portion, and a leg-accepting aperture extending along a front side of the therapeutic boot,
   b. a stabilization block configured to be removably coupled with the therapeutic boot and impede rotation of the therapeutic boot, and
   c. a fastener configured to couple the stabilization block with the limb.

10. The device according to claim 9, in which the stabilization block is elongated and generally trapezoidal in cross-section.

11. The device according to claim 9, in which the stabilization block is elongated and generally triangular in cross-section.

12. The device according to claim 9, in which the fastener comprises a pair of fastener elements spaced apart from each other.

13. The device according to claim 9, in which the fastener comprises at least one of a hook element and a loop element.

14. A device for stabilizing a limb, comprising:
   a. a therapeutic boot configured to receive and cushion the limb comprising a leg engaging portion, a foot engaging portion, and a leg-accepting aperture extending along a front side of the therapeutic boot,
   b. a stabilization block configured to be removably coupled with the therapeutic boot and impede rotation of the therapeutic boot,
   c. a tether secured to and extending from the stabilization block, the tether having a proximal surface and a distal surface, wherein the proximal surface is closer to the limb than the distal surface, and
   d. a fastener configured to secure at least one of the stabilization block and tether to the therapeutic boot, the fastener disposed on the proximal surface of the tether.

15. The device according to claim 14, in which the stabilization block is elongated and generally trapezoidal in cross-section.

16. The device according to claim 14, in which the stabilization block is elongated and generally triangular in cross-section.

17. The device according to claim 14, in which the fastener comprises a pair of fastener elements spaced apart from each other.

18. The device according to claim 14, in which the fastener comprises at least one of a hook element and a loop element.

* * * * *

EX PARTE REEXAMINATION CERTIFICATE (10763rd)

United States Patent
Ponsi et al.

(10) Number: US 8,435,199 C1
(45) Certificate Issued: Nov. 13, 2015

(54) THERAPEUTIC BOOTS STABILIZATION WEDGE

(75) Inventors: Lawrence G. Ponsi, Wheeling, IL (US); Jeffrey K. Crum, Cottageville, WV (US)

(73) Assignee: BARCLAYS BANK PLC, New York, NY (US)

Reexamination Request:
No. 90/013,230, May 7, 2014

Reexamination Certificate for:
Patent No.: 8,435,199
Issued: May 7, 2013
Appl. No.: 13/413,926
Filed: Mar. 7, 2012

Related U.S. Application Data

(63) Continuation of application No. 13/242,132, filed on Sep. 23, 2011, which is a continuation of application No. 11/855,560, filed on Sep. 14, 2007, now Pat. No. 8,535,255.

(51) Int. Cl.
A61F 5/00 (2006.01)
A61F 5/01 (2006.01)

(52) U.S. Cl.
CPC .................................. A61F 5/0111 (2013.01)

(58) Field of Classification Search
None
See application file for complete search history.

(56) References Cited

To view the complete listing of prior art documents cited during the proceeding for Reexamination Control Number 90/013,230, please refer to the USPTO's public Patent Application Information Retrieval (PAIR) system under the Display References tab.

*Primary Examiner* — Sara Clarke

(57) ABSTRACT

A device for stabilizing a limb, typically when the limb is in a therapeutic boot. A wedge-shaped stabilization block includes an outwardly-extending tether. A fastener in the form of spaced fastener elements is located on the tether for securing the stabilization block in place.

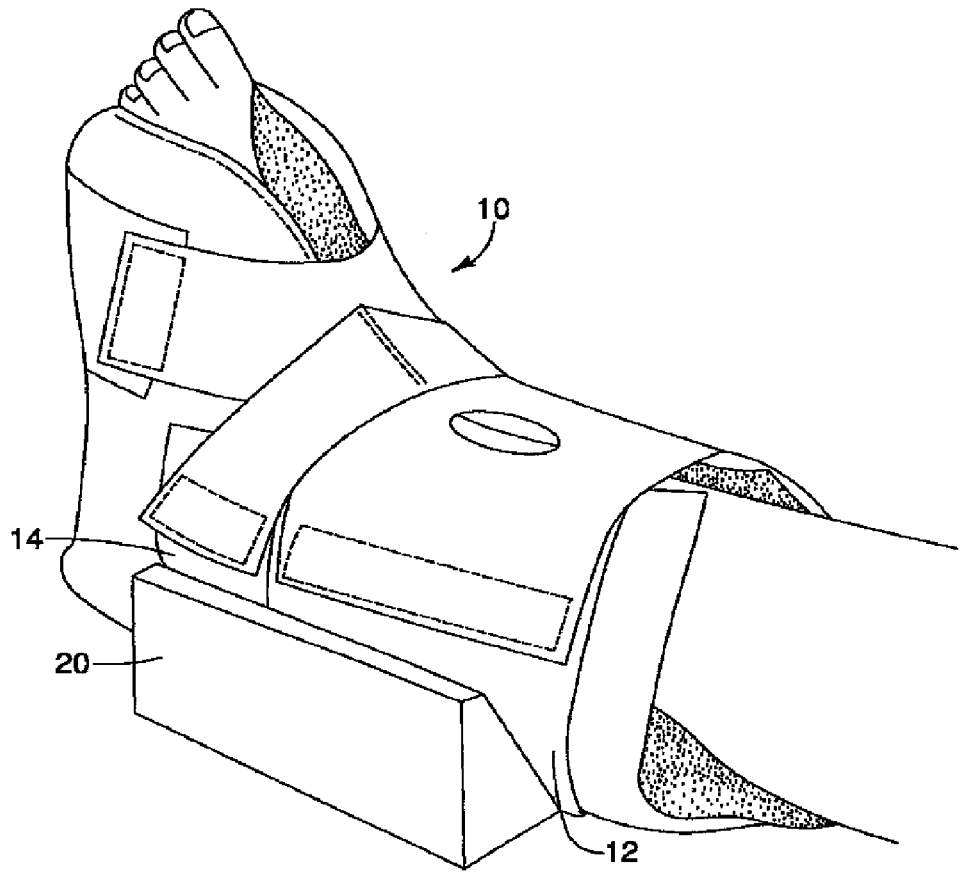

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 14-18 is confirmed.

Claims 9-13 are cancelled.

Claim 1 is determined to be patentable as amended.

Claims 2-8, dependent on an amended claim, are determined to be patentable.

1. A device for stabilizing a limb, comprising:
   a. a therapeutic boot configured to receive and cushion the limb comprising a leg engaging portion, a foot engaging portion, and a leg-accepting aperture extending along a front side of the therapeutic boot,
   b. a stabilization block configured to impede rotation of the limb,
   c. a tether secured to and extending from the stabilization block, the tether configured to be coupled with the [limb] *therapeutic boot*, and
   d. a fastener configured to couple the stabilization block with the therapeutic boot.

\* \* \* \* \*